(12) United States Patent
Teramoto

(10) Patent No.: US 7,792,240 B2
(45) Date of Patent: Sep. 7, 2010

(54) X-RAY CT APPARATUS

(75) Inventor: Fuyuhiko Teramoto, Nagarayama (JP)

(73) Assignee: Hitachi Medical Corporation, Tokyo (JP)

( * ) Notice: Subject to any disclaimer, the term of this patent is extended or adjusted under 35 U.S.C. 154(b) by 458 days.

(21) Appl. No.: 11/794,831

(22) PCT Filed: Jan. 17, 2006

(86) PCT No.: PCT/JP2006/300500

§ 371 (c)(1),
(2), (4) Date: Jul. 6, 2007

(87) PCT Pub. No.: WO2006/077815

PCT Pub. Date: Jul. 27, 2006

(65) Prior Publication Data

US 2008/0089465 A1  Apr. 17, 2008

(30) Foreign Application Priority Data

Jan. 18, 2005 (JP) ............................. 2005-009732

(51) Int. Cl.
*A61B 6/00* (2006.01)
(52) U.S. Cl. ........................................................ 378/8
(58) Field of Classification Search ............. 378/4, 378/8, 12
See application file for complete search history.

(56) References Cited

U.S. PATENT DOCUMENTS

| | | | | |
|---|---|---|---|---|
| 4,182,311 A | * | 1/1980 | Seppi et al. | .............. 600/428 |
| 5,602,891 A | * | 2/1997 | Pearlman | .................. 378/62 |
| 6,226,350 B1 | * | 5/2001 | Hsieh | ..................... 378/98 |
| 6,421,552 B1 | * | 7/2002 | Hsieh | ..................... 600/425 |
| 6,426,990 B1 | * | 7/2002 | Cesmeli | .................. 378/8 |
| 6,504,893 B1 | * | 1/2003 | Flohr et al. | ................ 378/8 |
| 2004/0120450 A1 | | 6/2004 | Flohr et al. | |
| 2004/0136501 A1 | * | 7/2004 | Boyd et al. | .............. 378/210 |

FOREIGN PATENT DOCUMENTS

| | | |
|---|---|---|
| EP | 1016376 A2 | 7/2000 |
| JP | 2000-210282 | 8/2000 |
| JP | 2004-121840 | 4/2004 |
| WO | WO02/41780 A2 | 5/2002 |

* cited by examiner

*Primary Examiner*—Edward J Glick
*Assistant Examiner*—Alexander H Taningco
(74) *Attorney, Agent, or Firm*—Cooper & Dunham LLP

(57) ABSTRACT

An X-ray CT apparatus in which phase information on a moving part of an object performing periodic motions is obtained externally, projection data corresponding to desired phase information out of the above phase information is stored while being associated therewith, that tomogram of the object corresponding to the desired phase information is reconstructed using the projection data corresponding to the desired phase information thus stored, a target tomogram is constructed by supplementing signal components lacking in the tomogram of the object corresponding to the desired phase information with the signal components of the tomogram of the object stored in a tomogram storage means, and then the target tomogram is displayed.

17 Claims, 5 Drawing Sheets

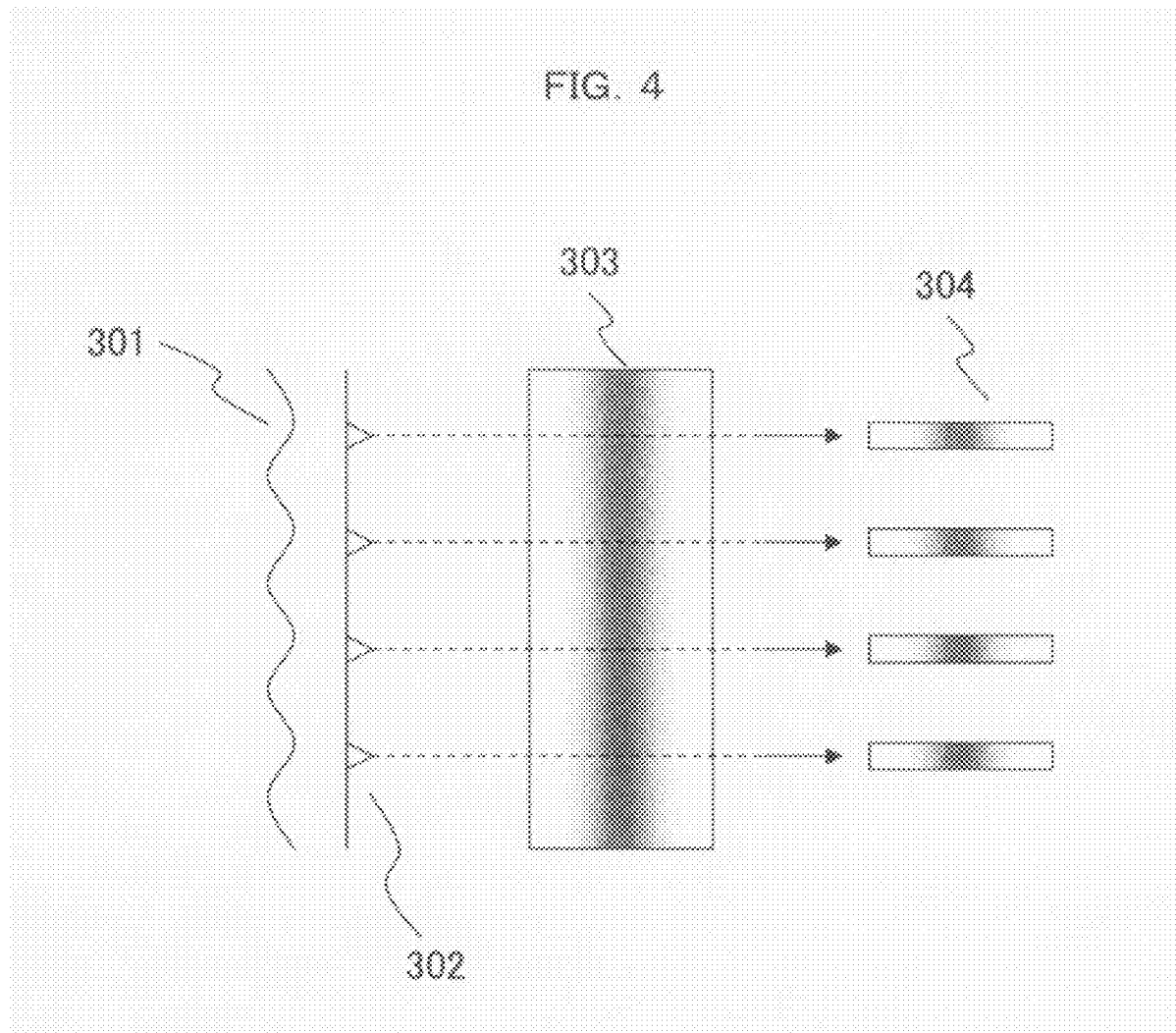

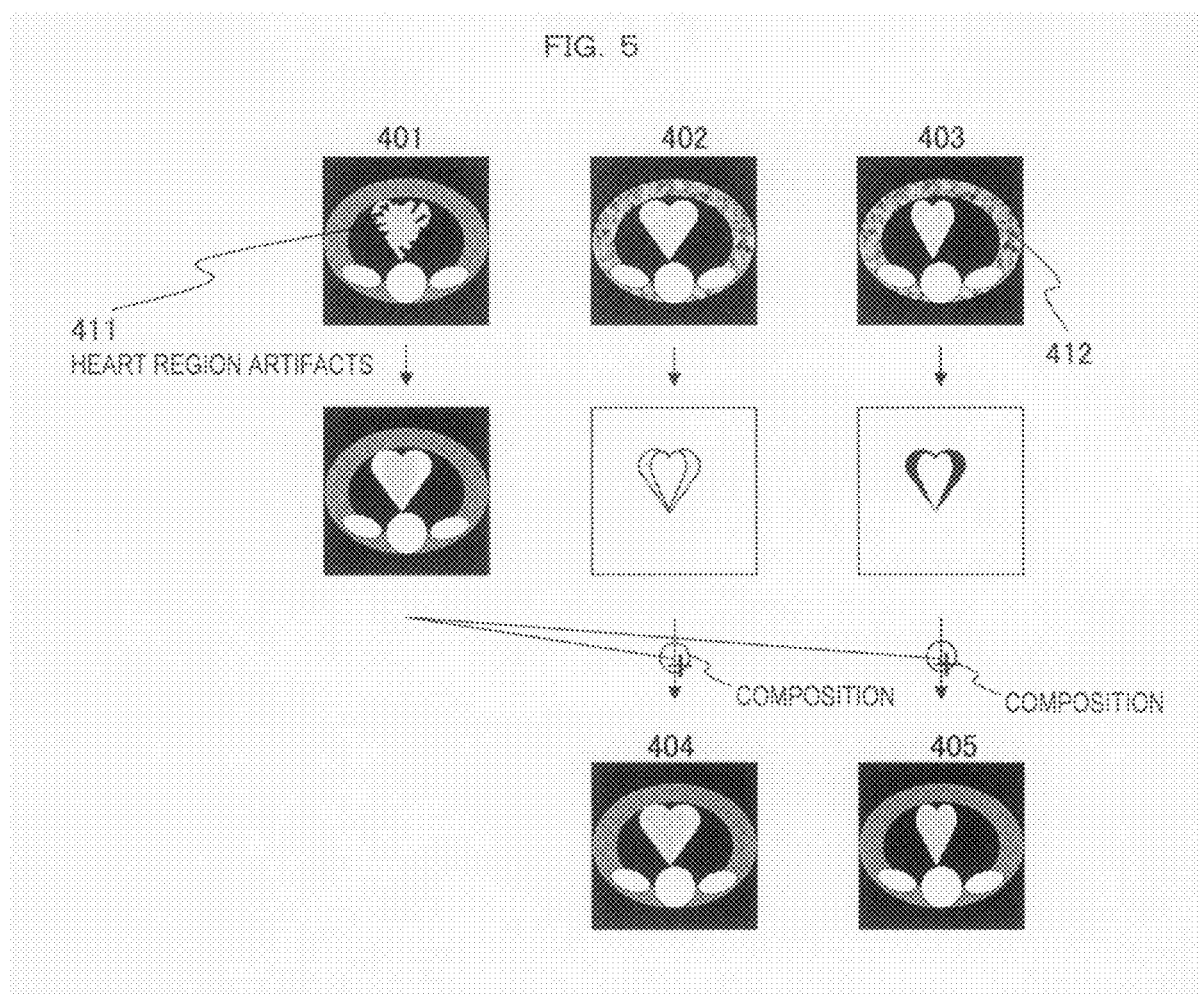

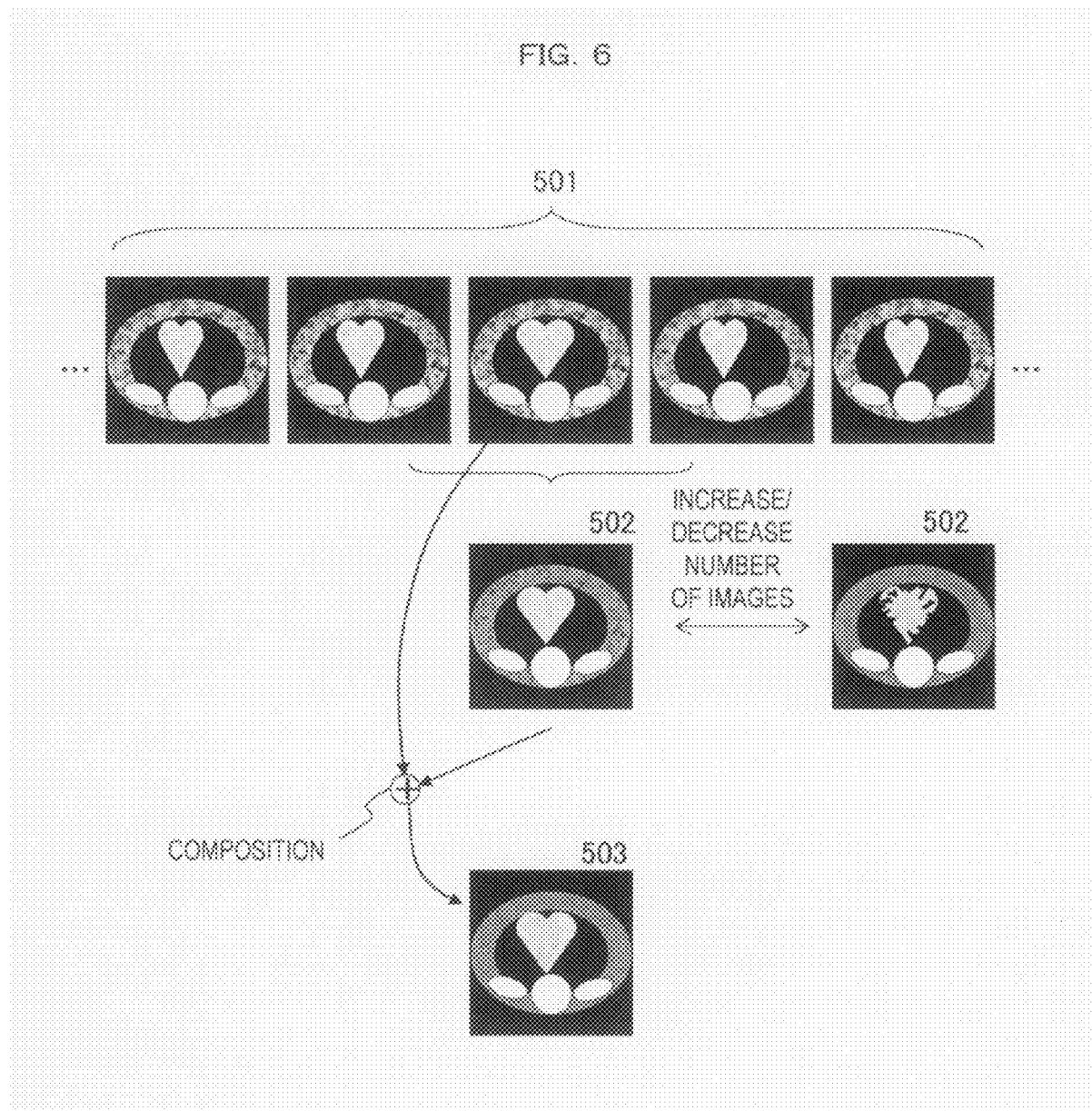

X-RAY CT APPARATUS

TECHNICAL FIELD

The present invention relates to a technique for reducing influence of artifacts to the tomogram of an object imaged by an X-ray CT apparatus caused by the moving region of the object (hereinafter referred to as movement artifacts), thus obtaining a high-quality tomogram. The present application accompanies the claim of priority in Paris, based on Japanese Patent Application No. 2005-009732 by Japanese Patent Law, and is to be incorporated by reference for receiving the benefit of Japanese Patent Application No. 2005-009732.

BACKGROUND ART

An X-ray CT apparatus is for obtaining a tomogram of an object by irradiating X-ray from an X-ray tube to the object while rotating the X-ray tube around the object, detecting projection data from various angle directions around the object by an X-ray detector, and performing image reconstruction calculation on the detected projection data.

In X-ray CT apparatus, there are occasions that the object moves while collecting projection data since the X-ray tube rotates around the object 180-360 degrees upon collecting projection data necessary for image reconstruction calculation. When the object moves, movement artifacts are generated which hinder the tomogram from being accurately reconstructed.

Since movement artifacts are notably generated especially upon setting a moving organ such as a heart that constantly repeats motion of expansion and contraction as the measurement region and they tend to be an obstacle to obtain the tomogram for diagnosis, various methods have been studied for the purpose of reducing them.

A technique to avoid movement artifacts is disclosed in Patent Document 1 as an example.

In this Document, a technique is described for reducing movement artifacts by applying ECG gate scan to a spiral scan, and interpolating discontinuity of projection data generated thereupon using, for example, data of heartbeat time phase in 180 degrees opposite relationship.

Patent Document 1: JP-A-2002-330961

However, there is a fear that the tomogram obtained by the previously mentioned method results in low quality, since the projection data used for this method was acquired in shorter time period compared to normal examination and the reconstruction of the tomogram is performed using the opposed beam data thereof, and therefore noise components are increased in the reconstructed tomogram. In other words, disclosed contents of Patent Document 1 cannot meet the needs for avoiding quality deterioration of the obtained tomogram.

Another method for preventing the above-mentioned influence to the image quality is to raise the energy of X-ray to a greater level than used in normal examination, but this will expose the object to more exposure to radiation. This method has no consideration for protecting the object from exposure to radiation.

BRIEF SUMMARY

In an aspect of this disclosure, there is provided an X-ray CT apparatus capable of improving the image quality without increasing exposure of the object to radiation.

An X-ray CT apparatus in an exemplary embodiment of the present invention comprises:

an X-ray tube for generating X-rays to irradiate an object to be examined;

an X-ray detector for measuring X-ray dosage transmitted through the object;

scanner means wherein the X-ray tube and the X-ray detector are mounted facing each other in a turntable, and the X-ray tube and the X-ray detector are rotated around the object;

projection data calculation means for calculating projection data of the object from the X-ray dosage measured by the X-ray detector at a rotation angle rotated by the scanner means;

reconstruction means for reconstructing a tomogram of the object using the calculated projection data;

tomogram storage means for storing the reconstructed tomogram of the object;

association storage means for externally obtaining the projection data calculated by the projection data calculation means and the phase information of a moving region of the object performing periodic motion, and storing the projection data corresponding to the desired phase information out of the above-obtained phase information while being associated with therewith;

target tomogram construction means for reconstructing the tomogram of the object corresponding to the desired phase information by the reconstruction means using the projection data corresponding to the desired phase information stored in the association storage means, and constructing a target tomogram by compensating for the signal components lacking in the tomogram of the object corresponding to the desired phase information by the signal components of the tomogram of the object stored in the tomogram storage means; and image display means for displaying the constructed target tomogram. The above-mentioned X-ray CT apparatus can restrain negative influence to the image quality and reduce radiation exposure of X-ray to the object.

BRIEF DESCRIPTION OF THE DIAGRAMS

FIG. 4 is an explanatory diagram related to the projection data collection of the ECG synchronized scanning related to the present invention.

FIG. 5 is a diagram showing an image composition related to the present invention.

FIG. 6 is a diagram showing image composition different from the one in FIG. 5.

DESCRIPTION OF THE SYMBOLS

101 . . . console, 102 . . . system bus, 103 . . . table, 104 . . . object, 105 . . . table controller, 106 . . . X-ray tube, 107 . . . X-ray detector, 108 . . . scanner controller, 120 . . . turntable, 109 . . . image processor, 110 . . . image displayer, 111 . . . magnetic disk, 112 . . . CPU, 113 . . . electrocardiograph, 302 . . . specified heartbeat time phase of the target, 401 . . . total phase tomogram, 402 . . . diastolic tomogram, 403 . . . systolic tomogram, 501 . . . tomogram of each phase, 502 . . . averaged tomogram, 503 . . . noise-reduced tomogram, 1091 . . . tomogram group creation means, 1092 . . . movement-degree acquisition means, 1093 . . . target image construction means.

BEST MODE FOR CARRYING OUT THE INVENTION

An embodiment of an X-ray CT apparatus of the present invention will be described referring to the diagrams.

In the diagrams used for the explanation of the present invention, the same symbols are encoded to the parts having the same function in all of the diagrams, and the description thereof will be omitted.

Embodiment 1

First, embodiment 1 related to the present invention will be described.

Figure 1:
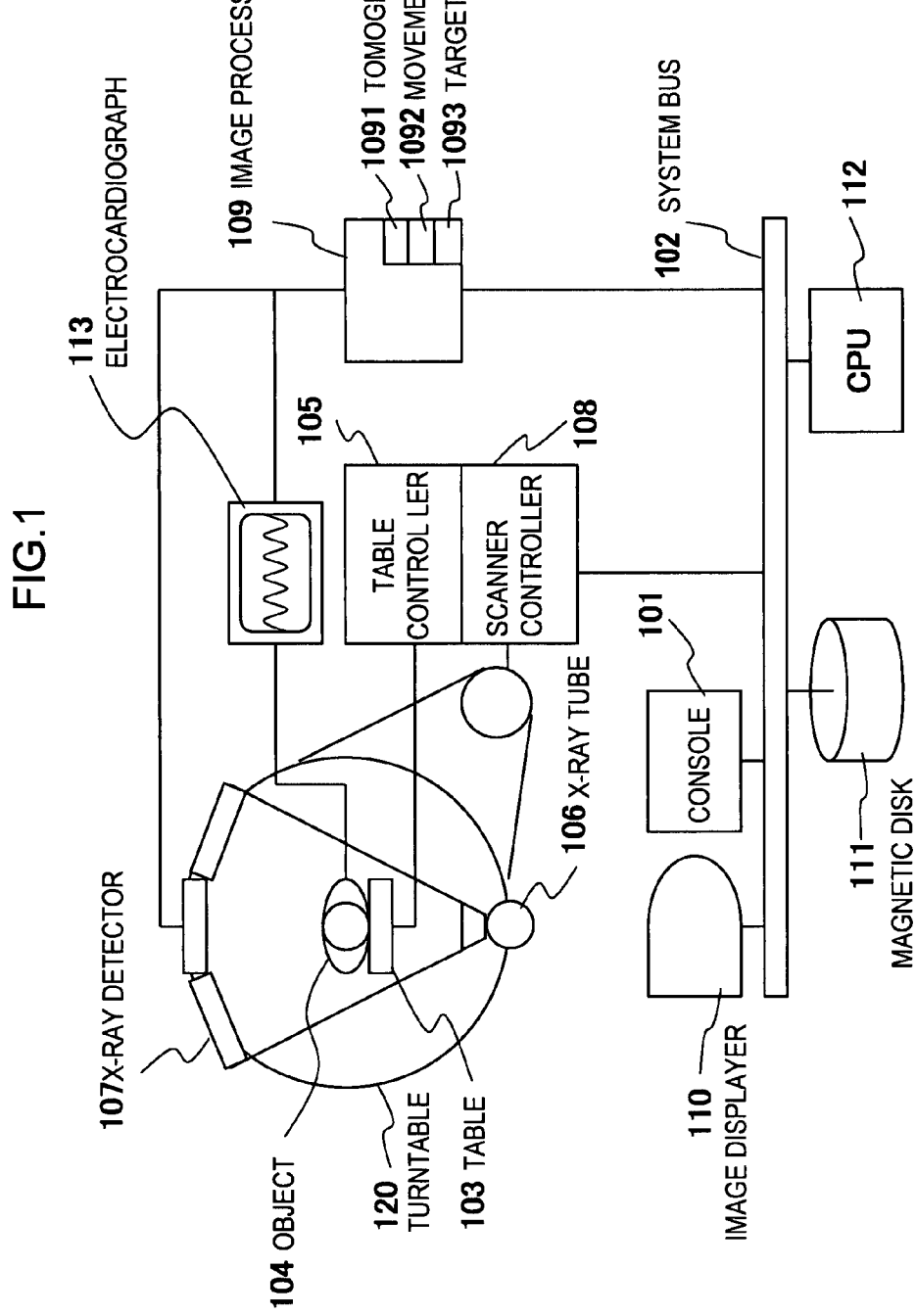
FIG. 1 is a diagram showing a configuration example of an X-ray CT apparatus to which the present invention is applied.

FIG. 1 is a diagram showing the configuration example of the X-ray CT apparatus to which the present invention is applied.

The X-ray CT apparatus has scanner controller 108, image processor 109, image displayer 110, magnetic disk 111 and CPU 112 being connected to console 101 via system data transfer bus (hereinafter referred to as a system bus) 102, table controller 105 being connected to table 103, X-ray tube 106 and X-ray detector 107.

Console 101 is for an operator (radiologic technologist, etc.) to perform input operation of data such as measurement condition setting. Object 104 is placed laying down on table 103, and transferred to the scanning position (hereinafter referred to also as a region) by table controller 105. In table controller 105, control amount is set according to the measurement condition inputted by the operator via the console. X-ray by which the control amount is set according to the measurement condition inputted through console 101 is generated by X-ray tube 106, and is eradiated to object 104. The X-ray transmitted through object 104 is measured by X-ray detector 107. X-ray tube 106 and X-ray detector 107 are arranged in turntable 120 facing each other. Rotation of turntable 120 is controlled by scanner controller 108. Accordingly, projection data necessary for obtaining a tomogram of object 104 can be measured. Projection data measured by X-ray detector 107 is transferred to image processor 109. In image processor 109, a tomogram of object 104 is constructed by the image reconstruction calculation. Also, tomogram group creation means 1091, movement-degree acquisition means 1092 and target image creation means 1093 are included in image processor 109 which will be described later.

Data of the constructed tomogram is transferred to image displayer 110 via system bus 102. Data of the transferred tomogram is displayed on image displayer 110. Also, these tomograms are stored in magnetic disk 111 as need arises. The series of operations of the above-mentioned respective devices are generally controlled and regulated by CPU 110.

Meanwhile, projection data is, when a periodically moving organ such as a heart is in the measurement range of the object, stored while being associated with the phase wherein the cycle of the heart is separately measured. In other words, as for the examination for constructing a tomogram of the specified heartbeat time phase, ECG 113 is connected to the object, measurement data such as ECG waveform is transferred to image processor 109 upon being measured, and the phase of the cycle is associated with the projection data and stored in a memory such as magnetic disk 111 so that they can be used for the image processing to be performed in image processor 109. In the explanation below, a heart will be cited as the periodically moving organ of the object.

Next, the image processing procedure to be performed in image processor 109 controlled by the above-mentioned CPU 112 will be described referring to FIG. 2.

Figure 2:
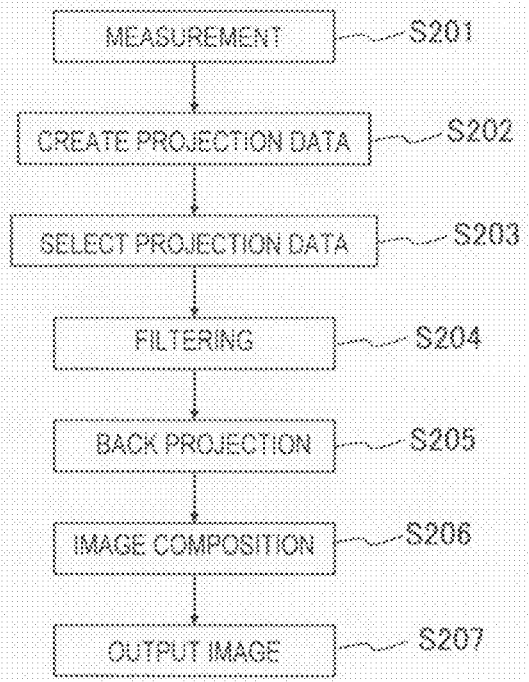
FIG. 2 is a flow chart of the image processing relating to the present invention.

FIG. 2 is a flow chart of the image processing related to the present invention.

X-ray measurement (CT scan) is performed by irradiating X-ray to object 104 from X-ray tube 106 while rotating X-ray 106 and X-ray detector 107 and detecting the transmitted X-ray of object 104 by X-ray detector 107. Such measured data of X-ray dosage is transferred to image processor 109 (Step S201).

Creation process of the projection data is performed by image processor 109 on X-ray dosage data being transferred in the above-mentioned step. Data of transmitted X-ray dosage is converted into logarithmic function to make it into projection data in order to present exponential damping characteristic (Step S202).

The operator selects the projection data necessary for constructing a tomogram at the specific heartbeat time phase through input operation of console 101. The heartbeat time phase upon acquiring the selected projection data is measured upon scanning using an electrocardiograph 113, and stored in magnetic disk 111. At this time, selection of the projection data is carried out according to two conditions. The first condition is to select data at a heartbeat time phase intended to be reconstructed. The second condition is that the projection data is continued for at least 180 degrees (Step S203).

Figure 3:
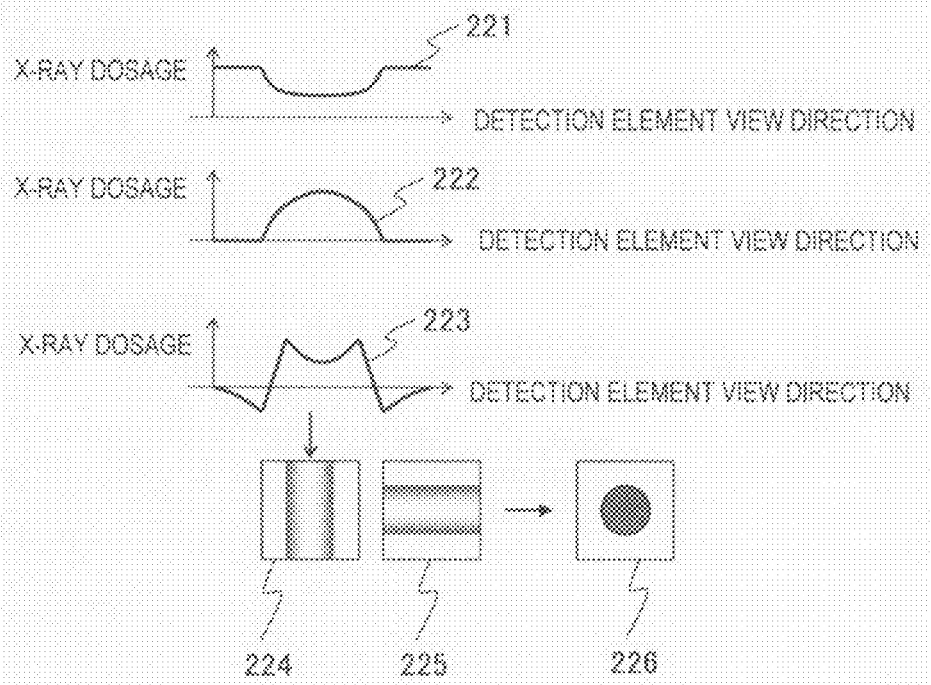
FIG. 3 is an explanatory diagram of image reconstruction relating to the present invention.

Filtering is performed on the projection data for reshaping it by distribution of X-ray absorption rate by image processing calculation device 109. The reshaping of the projection data is performed as illustrated in FIG. 3. FIG. 3 is a diagram for explaining the image reconstruction related to the present invention. Data of the transmitted X-ray dosage before the reshaping has smooth curve on both ends of the object as seen in 221 of FIG. 3. When projection data is converted from data of the transmitted X-ray dosage before being reshaped, the value gets higher as it moves closer to the center of the object as seen in 222 of FIG. 3, whereby the projection data is in a condition of not being reflected by the X-ray absorption rate. When a tomogram is reconstructed from the projection data before being reshaped, it exerts an influence on the image quality of both ends of the object. Given this factor, the projection data is reshaped by filtering before the back projection process so that the value gets closer to the precise distribution of the X-ray absorption rate. 223 of FIG. 3 indicates the data after filtering. After filtering, the data equivalent to the distribution of X-ray absorption rate can be obtained (Step S204).

The back projection process is performed on the projection data after filtering. Back projection is a process to keep adding projection data to all of the pixels of the path from which the projection data are obtained. 224 and 225 of FIG. 3 indicate the diagrams wherein the projection data after being filtered is executed with back projection from each of two orthogonal directions (Step S205)

On the back projected data, image processing considering the heartbeat time phase and the construction of the tomogram from which the noise is reduced are carried out. By superposing the back-projected data in FIG. 3, the final reconstructed image is completed. Step S206 will be described in detail later (Step S206).

The tomogram reconstructed in step S206 is outputted to image displayer 110. Here, the tomogram means an image wherein the arrangement of the digitalized data of X-ray absorption rate called CT value are reconstructed (Step S207).

Next, the content of step 203 "select projection data" in FIG. 2 will be described in detail referring to FIG. 4. FIG. 4 is a diagram of the projection data for selecting specified heartbeat phase. Condition of the heartbeat measured in real time upon projection data measurement is determined by ECG data 301. Specified heartbeat phase 302 being the target for reconstruction denotes the phase within one cycle of periodic heartbeat. Specified heartbeat phase 302 represents what percentage it occupies within the interval between R-waves. Here, from projection data 303, only specified phase projection data 304 corresponding to specified-heartbeat time phase 302 are abstracted along measurement time axis. Specified phase projection data 304 is abstracted a plurality of times over a plurality of heartbeats, and the plurality of abstraction is repeated until they become the data of continued range of at least 180 degrees which is necessary for back projection. The tomogram of the specific phase is thus constructed through performing process such as filtering, back projection, image composition and image output described in steps S204~S207 in FIG. 2 on the obtained projection data of the specific phase.

Next, step S206 "image processing and construction of tomogram" in FIG. 2 will be described referring to FIG. 5. FIG. 5 is a diagram showing the image composition related to the present invention. In the case that the image construction is carried out without considering the heartbeat time phase, artifacts 411 as seen in 401 of FIG. 5 are generated in the region having large motion due to a heartbeat. Therefore, the tomogram having artifacts 411 is not appropriate for diagnosis since it is not accurate.

On the other hand, in the case that the heartbeat time phase is taken into consideration, generation of movement artifacts can be avoided by constructing a tomogram by collecting projection data 304 of the specific phases in FIG. 4. For example, more precise condition of the heart in each phase can be reconstructed by collecting the projection data of only diastole for a heartbeat phase in diastole as seen in diastolic tomogram 402, and collecting the projection data of only systole for a heartbeat phase in systole as seen in systolic tomogram 403.

However, in this case, since incident X-ray dosage is not enough to obtain a high quality tomogram, image noise 412 often generated.

Given this factor, in the present embodiment example, the tomogram straddling over a plurality of phases is constructed at the same time upon construction of the reconstructed image in the target heartbeat time phase. Here, image processor 109 has:

tomogram group creation means 1091 capable of creating a plurality of tomogram groups wherein one or more tomograms constructed in projection data 304 of specific phases are summed;

movement-degree acquisition means 1092 for obtaining the degree of movement of the pixel value corresponding to the phase on the cycle of each pixel of the target image to be finally displayed; and target image construction means 1093 for constructing a tomogram of the target heartbeat time phase using the plurality of tomogram groups created based on the degree of the movement of the pixel value obtained by movement-degree acquisition means 1092. Movement-degree acquisition means 1092 also has a function to judge the degree of movement in each pixel. The principle of the above-mentioned judgment is that the degree of the movement can be judged from the difference between CT values among the phases, since the CT value should not vary by the heartbeat time phase in places having small movement.

An example for the concrete acquisition of movement degree in each pixel to be exemplified here is the case, for example, that the movement degree for total of 10 heartbeat time phases are obtained at 10% of each time phase. When it is set that the arrangement of CT value of the tomogram at heartbeat phase i=0, 10, . . . , 90(%) is Di[x,y] (x and y indicate coordinate of the pixel), movement degree at pixel x and y (M[x,y]) can be determined by "maximum value−minimum value" as expressed in [formula 1].

$$M[x, y] = \max(D0[x, y], D10[x, y], \ldots, D90[x, y]) - \min(D0[x, y], D10[x, y], \ldots, D90[x, y])$$ [Formula 1]

Also, movement degree can be determined using variance value or standard deviation value as expressed in [formula 2] and [formula 3].

$$V[x, y] = (D0[x, y] - m[x, y])^2 + (D10[x, y] - m[x, y])^2 + \ldots + (D90[x, y] - m[x, y])^2$$ [Formula 2]

Here, $m[x, y] = (D0[x, y] + D10[x, y] + \ldots + D90[x, y])/10$ $$\sigma[x, y] = \sqrt{V}[x, y]$$ [Formula 3]

Thus obtained movement degree is compared with a threshold value that is set separately. The threshold value may be set empirically by an operator via console 101, or may set by database, after making database of the value being set in conventional manner. As for the pixels having smaller movement degree than the threshold, the pixels of the reconstructed image straddling over all the phases (set as Da[x,y]) are used. Contrarily, as for the pixels having larger movement degree than the threshold, the pixels of the image at the target heartbeat time phase are set for using as the pixels for constructing the composition image.

In other words, pixels Di[x,y] of the image at the target heartbeat time phase are preferentially used for the movement degree of the respective pixels, and the movement degree for the respective pixels are determined by movement-degree acquisition means 1092. By replacing the pixels having smaller movement degree than the predetermined threshold with the corresponding pixels in the total phase tomogram, diagnostic images are composed by target image construction means 1093, whereby enabling construction of high-quality images.

In concrete terms, by synthesizing the region having small movement degree of the previously described total phase tomogram 401 and the region having large movement degree of diastolic tomogram 402 or systolic tomogram 403, diastole noise-reduced tomogram 404 or systolic noise-reduced tomogram 405 are synthesized by target image construction means 1093.

Previously mentioned total phase image 401 may be constructed by summing projection data of all heartbeat time phases by target image construction means 1093. Also, each movement degree corresponds to a difference value, standard deviation value and variance value, which may be set in accordance with condition for reconstruction such as FOV, filtering parameter by the region, or age or predisponency of the object. And images of which more noise is reduced can be obtained by setting empirically accumulated values for the above-mentioned condition for reconstruction. For this reason, as for the threshold value, it is desirable that at least one parameter mentioned above is set variable by the operator using a device such as console 101.

Embodiment 2

Embodiment 2 related to the present invention will now be described. In embodiment 2, procedure up to the usage of the total phase tomogram and diastolic tomogram 402 or systolic tomogram 403 in FIG. 5 is the same as embodiment 1, thus the description thereof will be omitted.

In embodiment 1, movement degree was determined by variance value or standard deviation value as seen in [formula 2] or [formula 3] as a criterion for the pixels to use for synthesis.

In embodiment 2, it is different from embodiment 1 in a point that a criterion for evaluation as expressed in [formula 4] is used for the degree of movement. More specifically, pixels Da[x,y] of the image including all phases and the arrangement Di[x,y] of CT value of the tomogram at heart-beat time phase=0, 10, . . . , 90(%) are weighted and summed in compliance with movement degree of the respective pixels in [formula 4].

In this formula, in order to divide by occasions, the degree of weighted addition is changed by using weighted two threshold values T1 and T2. However, the number of the threshold value can be three and more, and the weight can be changed along with the number of threshold.

If $\sigma[x,y] < T1$, $Di'[x,y] = Da[x,y]$

If $T1 \leq \sigma[x,y] < T2$, $Di'[x,y] = w*Di[x,y] + (1-w)*Da[x,y]$

Here, $w = (\sigma[x,y] - T1)/(T2 - T1)$

If $T2 \leq \sigma[x,y]$, $Di'[x,y] = Di[x,y]$ [Formula 4]

In addition, in the present embodiment, since the movement degree is determined by a plurality of threshold values, it is possible to further reduce noise of portions having intermediate movement.

Embodiment 3

Embodiment 3 related to the present invention will now be described. Embodiment 3 has basically the same configuration as embodiments 1 and 2. Unless otherwise mentioned, reference numbers used in this embodiment are also the same as embodiments 1 and 2.

The method for image composition of the embodiment 3 will be described referring to FIG. 6. FIG. 6 is a diagram showing the image composition different from FIG. 5. In the diagram, 501 indicates the tomograms in each phase, 502 indicates the averaged tomograms, and 503 indicates the noise-reduced tomogram.

In this diagram, for example, 10 pieces of tomograms 501 are constructed, one in each phase with 10% intervals of the heartbeat time phase based on the target phase. In this embodiment, by averaging the tomograms of not all phases but the target phase and the phases in the vicinity of 10% thereof, averaged tomogram 502 to which 20% of phase range is increased is constructed by target image construction means 1093.

Thus constructed averaged tomogram 502 has less artifact compared to total phase tomogram 401 including the total phase shown in FIG. 5, and has less noise than tomograms 501 in each phase.

In the same manner, by increasing the number of images to be averaged, the tomogram group can be constructed wherein artifacts and noise are varied stepwise. It also is possible to set weighting factor such as k[i] upon averaging and calculate weighted average as expressed in [formula 5].

$Da[x,y] = \Sigma k[i]*Di[x,y]$ [Formula 5]

Noise-reduced tomogram 503 is constructed by target image construction means 1093 by selecting or interpolating the tomogram, with respect to each pixel, suitable for determination of the movement degree expressed in [formula 1]~[formula 3] out of the above-mentioned tomogram groups and synthesizing them.

Regarding such construction of noise-reduced tomogram 503, when tomograms of many phases are needed such as observing motion of a heart, tomograms of a plurality of phases can be outputted and the already obtained data of the tomogram of the plurality of phases can be used, thus comparatively efficient image construction can be carried out.

Also, since the image composition method of the present invention relates to the image display after the completion of the tomograms, it can be applied to various ECG synchronous scanning without being limited to the kind of detector, such as multi-row or single-row, or the variety of methods for tomogram construction in dependence upon the heartbeat time phases.

INDUSTRIAL APPLICABILITY

In accordance with the present invention, it is possible to reduce noise of not only the body surface region of the object, but also the regions having comparatively small motions but intended for detailed diagnosis such as a main artery or cardiac ventricle. According to the complexity of the object to be examined including its moving organs or motion regions as well as mixed portions having small or large motions, the present invention is capable of reducing all movement artifacts, exposure to radiation and noise of images having any size of motions.

The technique of the present invention can be applied widely to diagnosis of not only heartbeats, but also other movements such as respiratory movement.

The invention claimed is:
1. An x-ray CT apparatus comprising:
   an X-ray tube configured to generate X-rays for irradiating an object to be examined;
   an X-ray detector configured to measure an X-ray dosage transmitted through the object;
   a turntable configured to rotate the X-ray tube and the X-ray detector a specific rotation angle around the object, the x-ray tube and the x-ray detector being mounted facing each other on the turntable;
   projection data calculation means for calculating projection data of the object from the X-ray dosage measured by the X-ray detector;
   reconstruction means for reconstructing a tomogram of the object using the calculated projection data;
   tomogram storage means for storing the reconstructed tomogram of the object;
   association storage means for associating the projection data calculated by the projection data calculation means with a phase information of a moving region of the object having periodic motions, and storing both the phase information and the projection data associated with the phase information;
   target tomogram construction means for constructing a target tomogram of the object corresponding to desired phase information stored in the association storage means, and using the projection data associated with the desired phase information;

tomogram group creation means for creating a first tomogram group by summing at least one tomogram corresponding to the desired phase information, and a second tomogram group by summing at least one tomogram corresponding to other phase information different from the desired phase information of the first tomogram group; and movement-degree acquisition means for acquiring a degree of movement of a pixel value of each pixel of the target tomogram, wherein said target tomogram construction means constructs the target tomogram by performing weighting addition on the first and the second tomogram groups in each pixel according to the degree of movement of the pixel value acquired by the movement-degree acquisition means.

2. The X-ray CT apparatus according to 1, wherein the movement-degree acquisition means determines movement degree in each pixel by the deviance of the pixel value of the moving region.

3. The X-ray CT apparatus according to claim 2, wherein a threshold value for movement degree of the pixel value of the moving region is determined based on at least one of a difference value, maximum value, minimum value, variance value and standard deviation value of the movement quantity.

4. The X-ray CT apparatus according to claim 3, wherein the movement degree of the pixel value of the moving region is compared to the threshold value which is set separately, and a weighting factor for each of the first tomogram group and second tomogram group is set according to a result of the comparison.

5. The X-ray CT apparatus according to claim 3, wherein the movement degree of the pixel value of the moving region is compared to a plurality of threshold values.

6. The X-ray CT apparatus according to claim 1, wherein the tomogram group creation means creates the first tomogram group by summing at least two tomograms associated with the desired phase information stored in the association storage means, and creates the second tomogram group by summing at least two tomograms associated with phase information having a different cycle from the first tomogram group, and the target tomogram construction means constructs the target image by displacing the pixels of the second tomogram group with the pixels of the first tomogram group according to the movement degree of the pixel value acquired by the movement-degree acquisition means.

7. The X-ray CT apparatus according to claim 6, wherein the movement-degree acquisition means determines the degree of movement with respect to each pixel by deviance of the pixel value of the moving region.

8. The X-ray CT apparatus according to claim 7, wherein a threshold value with respect to movement degree of the pixel value of the moving region is determined based on at least one of a difference value, maximum value, minimum value, variance value and standard deviation value of the movement quantity thereof.

9. The X-ray CT apparatus according to claim 8, wherein the movement degree of the pixel value of the moving region is compared to the threshold value which is set separately, and a weighting factor or a displacement for each of the first tomogram group and second tomogram group is set according to a result of the comparison.

10. The X-ray CT apparatus according to claim 8, wherein the movement degree of the pixel value of the moving region is compared to a plurality of threshold values.

11. The X-ray CT apparatus according to claim 1, wherein the tomogram group creation means creates the first tomogram group by summing at least two tomograms associated with the desired phase information stored in the association storage means, and creates the second tomogram group by summing at least two tomograms associated with phase information having a different cycle from the first tomogram group, the target tomogram construction means includes averaged image calculation means for calculating an averaged tomogram based on the target tomogram to be constructed and the tomogram corresponding to the phase information of a cycle in the vicinity of the target tomogram, and the target tomogram construction means constructs the target image by performing weighting addition with respect to each pixel in accordance with the averaged tomogram.

12. The X-ray CT apparatus according to claim 11, characterized in further comprising means for setting the tomograms to be averaged by the averaged image calculation means at an arbitrary number.

13. The X-ray CT apparatus according to claim 1, wherein the tomogram group creation means creates the first tomogram group by summing at least two tomograms associated with the desired phase information stored in the association storage means, and creates the second tomogram group by summing at least two tomograms associated with phase information having a different cycle from the first tomogram group, the target tomogram construction means includes averaged image calculation means for calculating an averaged tomogram based on the target tomogram to be constructed and the tomogram corresponding to the phase information of a cycle in the vicinity of the target tomogram, and the pixels of the second tomogram group are displaced with the pixels of the first tomogram group in accordance with the averaged tomogram.

14. The X-ray CT apparatus according to claim 13, characterized in further comprising means for setting the tomogram averaged by the averaged image calculation means at an arbitrary number.

15. The X-ray CT apparatus according to claim 1, wherein the target tomogram construction means constructs the target tomogram using the reconstruction means, by reconstructing the tomogram of the object corresponding to the desired phase information using the projection data corresponding to the desired phase information stored in the association storage means while compensating signal components not in the tomogram of the object corresponding to the desired phase information with signal components of the tomogram of the object stored in the tomogram storage means.

16. The X-ray CT apparatus according to claim 1, wherein the tomogram group creation means creates the second tomogram group by summing tomograms corresponding to a plurality of respective phases.

17. The X-ray CT apparatus according to claim 16, wherein the target tomogram construction means constructs the target tomogram by using for each pixel, (i) a pixel value of the pixel from the first tomogram group if the pixel has a movement degree greater than a threshold value, and (ii) a pixel value of the pixel from the second tomogram group if the pixel does not have the movement degree greater than the threshold value.

* * * * *